(12) United States Patent
Chua

(10) Patent No.: US 11,458,231 B2
(45) Date of Patent: Oct. 4, 2022

(54) BREAST MILK COLLECTION AND STORAGE SYSTEM AND METHOD OF USE

(71) Applicant: Poh Leng Jeffrey Chua, Singapore (SG)

(72) Inventor: Poh Leng Jeffrey Chua, Singapore (SG)

(73) Assignee: MILLENNIUM ENTERPRISE PTE. LTD., Singapore (SG)

( * ) Notice: Subject to any disclaimer, the term of this patent is extended or adjusted under 35 U.S.C. 154(b) by 628 days.

(21) Appl. No.: 16/551,461

(22) Filed: Aug. 26, 2019

(65) Prior Publication Data
US 2021/0060221 A1  Mar. 4, 2021

(51) Int. Cl.
*A61M 1/06* (2006.01)

(52) U.S. Cl.
CPC ............ *A61M 1/066* (2014.02); *A61M 1/062* (2014.02); *A61M 2209/088* (2013.01); *A61M 2210/1007* (2013.01)

(58) Field of Classification Search
CPC ........ A61M 1/06; A61M 1/062; A61M 1/064; A61M 1/066; A61M 1/068; A61M 1/007; A61M 2210/1007; A61B 2018/00333; A61J 13/00; A61J 9/0684; A61J 9/06; A61J 9/063; A61J 9/0615; A61J 9/08; A61J 9/085; B65D 85/80
See application file for complete search history.

(56) References Cited

U.S. PATENT DOCUMENTS

| | | | |
|---|---|---|---|
| 2,389,390 A | * | 11/1945 | Silverman ............ A61J 9/0615 248/102 |
| 2,500,786 A | * | 3/1950 | Austin ...................... A61J 9/08 220/592.27 |

(Continued)

FOREIGN PATENT DOCUMENTS

| | | |
|---|---|---|
| CA | 184104 | 9/2019 |
| CN | 303890343 A | 10/2016 |
| CN | 303890427 S | 11/2016 |

OTHER PUBLICATIONS

Chua, Poh Leng, Jeffrey, Design Patent Application entitled "Manual Breast Pump", filed Sep. 15, 2018, U.S. Appl. No. 29/663,465.

(Continued)

*Primary Examiner* — Bhisma Mehta
*Assistant Examiner* — William R Frehe

(57) ABSTRACT

A breast milk collection and storage system is disclosed that comprises a manual breast pump. The manual breast pump comprises a breast cup configured to engage with a mother's breast. The breast cup comprises an opening. The manual breast pump also comprises a reservoir at a base of the breast cup configured to receive breast milk through the opening and collect breast milk extracted from the mother's breast. The breast milk collection and storage system also comprises a stopper configured to seal the opening to prevent leakage of breast milk from the reservoir. The breast milk collection and storage system further comprises a capsule configured to enclose the manual breast pump with the (Continued)

stopper and apply a compression force to the stopper to maintain the seal of the opening when the capsule is closed.

18 Claims, 15 Drawing Sheets

(56) References Cited

U.S. PATENT DOCUMENTS

| | | | | |
|---|---|---|---|---|
| 2,733,710 | A * | 2/1956 | Zibell | A61J 9/08 383/110 |
| 4,076,139 | A * | 2/1978 | Larson | A61J 9/08 220/605 |
| 8,845,604 | B2 * | 9/2014 | Croizat | A61M 1/90 604/174 |
| D808,006 | S | 1/2018 | Zhang | |
| D810,925 | S | 2/2018 | Zhang | |
| 2009/0166310 | A1 * | 7/2009 | Cote | A61J 9/08 215/11.6 |
| 2013/0299443 | A1 * | 11/2013 | Stewart | A61J 9/0607 215/11.6 |
| 2018/0055262 | A1 * | 3/2018 | Vogel | F16M 13/02 |
| 2019/0175801 | A1 * | 6/2019 | Levine | A61M 1/064 |

OTHER PUBLICATIONS

Chua, Poh Leng, Jeffrey, Design Patent Application entitled "Manual Breast Pump Capsule and Strap", filed Aug. 26, 2019, U.S. Appl. No. 29/703,314.

Chua, Poh Leng, Jeffrey, EP Design Patent Application entitled "Capsule for Silicone Breast Pump", filed on Sep. 12, 2019, Serial No. 006861837-0001.

Chua, Poh Leng, Jeffrey, EP Design Patent Application entitled "Capsule for Silicone Breast Pump", filed on Sep. 12, 2019, Serial No. 006861837-0002.

Chua, Poh Leng, Jeffrey, EP Design Patent Application entitled "Capsule for Silicone Breast Pump", filed on Sep. 12, 2019, Serial No. 006861837-0003.

Chua, Poh Leng, Jeffrey, EP Design Patent Application entitled "Strap for Silicone Breast Pump", filed on Sep. 12, 2019, Serial No. 006859468-0001.

Chua, Poh Leng, Jeffrey, Patent Application entitled "Manual Breast Pump and Method of Use", filed Sep. 15, 2018, U.S. Appl. No. 16/132,362.

Chua, Poh Leng, Jeffrey, European Design Patent Application entitled "Silicone Breast Pump", filed on Sep. 7, 2018, Serial No. 005633328-0002.

Chua, Poh Leng, Jeffrey, Chinese Design Patent Application entitled "Silicone Breast Pump", filed on May 4, 2018, Serial No. 201830197234.9.

Babytree: Manual Breast Pump Listing; Retrieved from URL: http://www.babytree.com/commnity/club201400/topic_201912410.html (published on May 28, 2014).

Funny Baby: Eight Yuan poly cost-effective full silicone natural breast pump; retrieved from URL: http://product.800400.net/detail/7816236.html (published on Dec. 18, 2014).

* cited by examiner

BREAST MILK COLLECTION AND STORAGE SYSTEM AND METHOD OF USE

BACKGROUND

Nursing mothers often use breast pumps to express milk from their breasts for bottle feeding their infant children. Breast pumps may be manually or electrically operated.

SUMMARY

In one embodiment of the disclosure, a breast milk collection and storage system is disclosed. The breast milk collection and storage system comprises a manual breast pump. The manual breast pump comprises a breast cup configured to engage with a mother's breast. The breast cup comprises an opening. The manual breast pump also comprises a reservoir at a base of the breast cup configured to receive breast milk through the opening and collect breast milk extracted from the mother's breast. The breast milk collection and storage system additionally comprises a stopper configured to seal the opening to prevent leakage of breast milk from the reservoir. The breast milk and storage system further comprises a capsule configured to enclose the manual breast pump with the stopper and apply a compression force to the stopper to maintain the seal of the opening when the capsule is closed.

In another embodiment of the disclosure, a method of using a breast milk collection and storage system is disclosed. The method comprises engaging a breast cup of a manual breast pump with a breast of a mother. The breast cup comprises an opening. The method also comprises compressing and releasing a reservoir of the manual breast pump to create a suction force to extract breast milk from the breast through the opening into the reservoir and inserting a stopper into the opening to create a seal of the opening to prevent leakage of breast milk from the reservoir. The method further comprises closing a capsule around the manual breast pump with the stopper inserted and retaining the seal of the opening when the capsule is closed.

In yet another embodiment of the disclosure, a breast milk collection and storage kit is disclosed. The breast milk collection and storage kit comprises a manual breast pump. The manual breast pump comprises a breast cup configured to engage with a mother's breast. The breast cup comprises an opening. The manual breast pump also comprises a reservoir at a base of the breast cup configured to receive breast milk through the opening and collect breast milk extracted from the mother's breast. The breast milk collection and storage kit also comprises a stopper configured to seal the opening to prevent leakage of breast milk from the reservoir. The breast milk collection and storage kit further comprises a capsule configured to enclose the manual breast pump with the stopper and maintain the seal of the opening.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
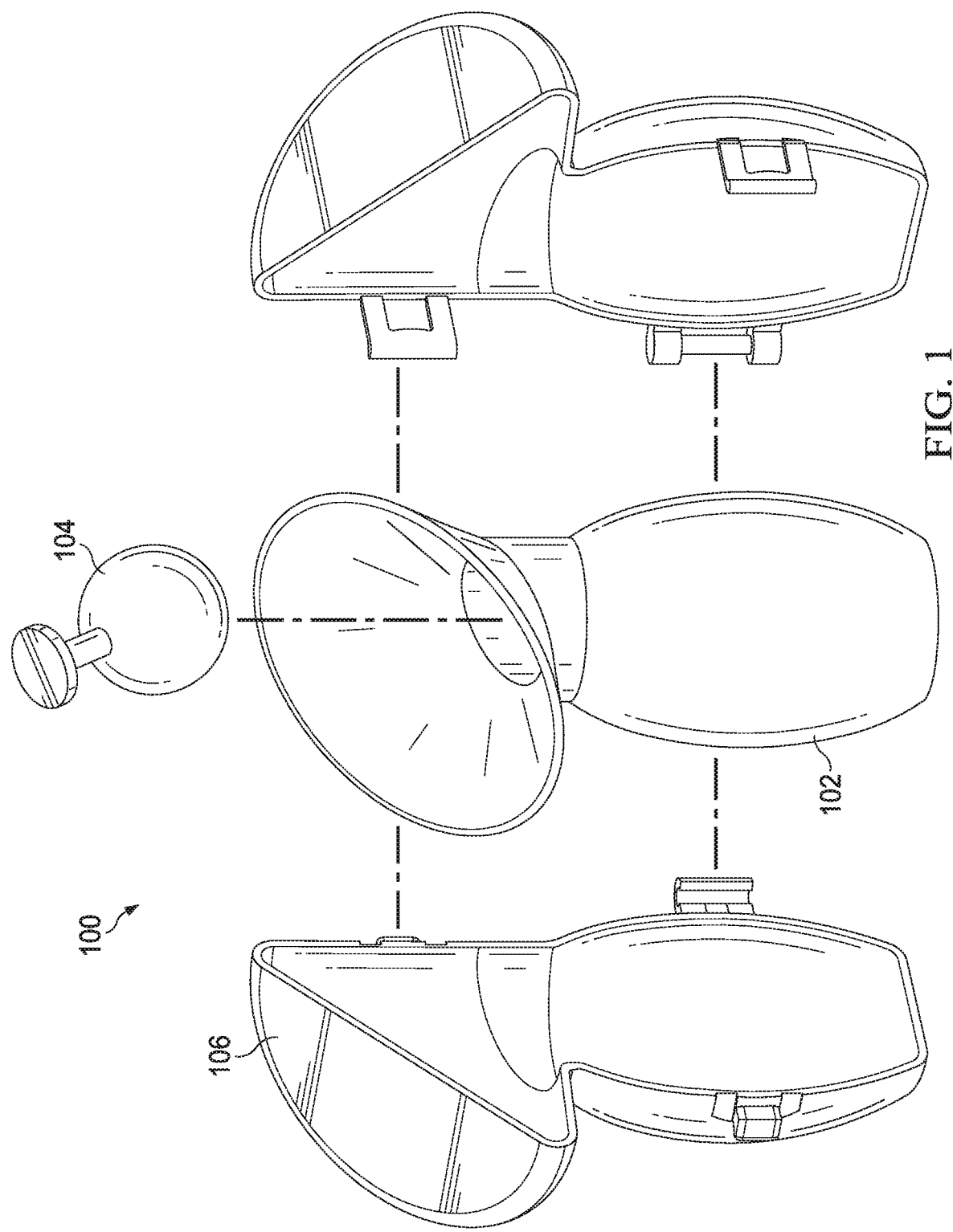
FIG. 1 illustrates an exploded view of a breast milk collection and storage system according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

Breast milk may be collected by and stored temporarily in a manual breast pump. To minimize the chances of the stored breast milk leaking from the manual breast pump, a stopper may be used to seal the opening of the manual breast pump. However, the stopper may be bumped or hit and become dislodged from the opening, causing the seal of the opening to be broken and breast milk to leak out of the manual breast pump. Further, some manual breast pumps are made of pliable material such as a polymer. If such a manual breast pump is compressed when the stopper is inserted in the opening, the pressure created by such compression may cause the stopper to become dislodged from the opening, causing the seal of the opening to be broken and breast milk to leak out of the manual breast pump. Thus, the pending disclosure is directed to a breast milk collection and storage system that helps to prevent the leakage of breast milk from the manual breast pump as well as keep the manual breast pump clean.

The breast milk collection and storage system disclosed herein comprises a manual breast pump, a stopper, and a capsule or storage container. The manual breast pump comprises a breast cup and a reservoir at the base of the breast cup. Breast milk is received into the reservoir through an opening in the breast cup. The opening of the breast cup is sealed by a stopper. To prevent the stopper from becoming dislodged from the opening of the breast cup and to maintain the seal, the manual breast pump and the stopper sealing the opening are enclosed by a capsule. The capsule may be made of a stiffer material than the manual breast pump. For example, the capsule may be made of a hard plastic. Such a construction of the capsule helps to ensure that while the manual breast pump and stopper are enclosed in the capsule, the manual breast pump cannot be compressed causing the stopper to become dislodged from the opening. In some embodiments, the capsule may apply a compression force to the stopper when the capsule is closed. This compression force can help to further maintain the seal of the opening and prevent the leakage of the breast milk from the manual breast pump. The enclosure of the manual breast pump within the capsule can also help to keep the manual breast pump clean by minimizing its exposure to elements in the environment.

The breast milk collection and storage system may also comprise a strap to help prevent leakage of breast milk from the manual breast pump during use of the manual breast pump. The strap may secure the manual breast pump to the mother during use so that the manual breast pump does not drop from the mother's breast (e.g., when a baby kicks the manual breast pump) and leak breast milk from the manual breast pump. For example, the mother may secure one end of the strap around the manual breast pump and place the other end of the strap around her neck while she uses the manual breast pump. The strap may include a double loop of straps (one big strap for around a mother's neck and one small strap for around a neck of the manual breast pump) with two adjustable knobs, clips, sliders, or fasteners. The main loop may be placed around a mother's neck and adjusted via a slider to enable the mother to align the manual breast pump with her breast. The second loop may be placed around the neck of the manual breast pump and adjusted via fastener to secure the second loop around the manual breast pump.

Turning now to FIG. 1, an embodiment of a breast milk collection and storage system 100 is illustrated. The breast milk collection and storage system 100 may comprise a manual breast pump 102, a stopper 104, and a capsule 106. As will be discussed in more detail below, the breast milk collection and storage system 100 may be used to prevent leakage of breast milk from the manual breast pump as well as keep the manual breast pump clean. The manual breast pump 102 will be discussed in more detail with reference to FIGS. 2 and 3, the stopper 104 will be discussed in more detail with reference to FIGS. 4 and 5, and the capsule 106 will be discussed in more detail with reference to FIGS. 6A-6E and 7. Although not illustrated in FIG. 1, in an embodiment, the breast milk collection and storage system 100 also comprises a strap, which will be discussed in more detail with reference to FIGS. 9 and 10.

Figure 2:
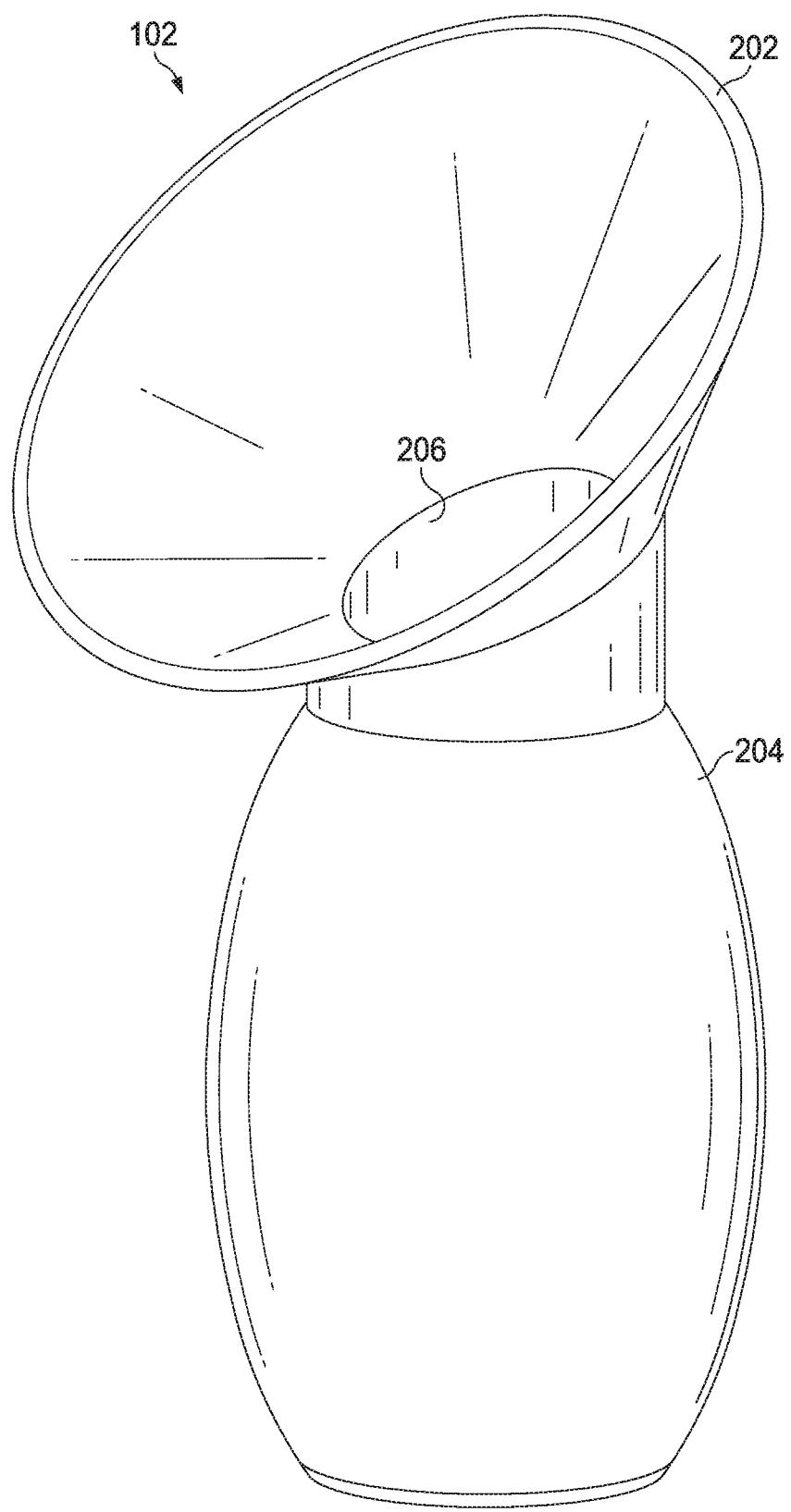
FIG. 2 illustrates a perspective view of a manual breast pump according to an embodiment of the disclosure.

Turning now to FIG. 2, an embodiment of the manual breast pump 102 having a breast cup 202 and a reservoir 204 is illustrated. The breast cup 202 may be shaped so as to enclose a volume defining the reservoir 204 used to receive and store any expressed breast milk. The breast cup 202 may comprise a funnel shape, cone shape, or another shape to engage with a mother's breast. The breast cup 202 comprises an opening 206 through which the expressed breast milk travels to the reservoir 204. The reservoir 204 may comprise a rounded shape to allow the restoring forces to restore the initial shape of the reservoir 204 when it is compressed. In some embodiments, the reservoir 204 may comprise a cylindrical shape, a spherical shape, a bulbous shape, a square shape, or another shape. The bottom of the reservoir 204 may have a flat surface to allow the breast pump 102 to be freestanding when placed on a flat surface.

In an embodiment, the reservoir 204 is at a base of the breast cup 202. The breast cup 202 and the reservoir 204 may be formed as a single unit (e.g., an integrated structure, etc.). A single unit manual breast pump is simpler and has fewer parts, making it easier to use and clean. In an alternative embodiment, the breast cup 202 and the reservoir 204 may be individual components coupled together.

The breast cup 202 and the reservoir 204 may be made of pliable material such as a polymer. Various food grade polymers can be used such as silicone. The material used to form the manual breast pump 102 may have any color or patterns as desired, and in some embodiments may be clear. This may allow the volume of collected breast milk to be easily determined, for example, by using markings or graduations on the interior or exterior of the reservoir 204 to measure the volume.

In an embodiment, the polymer can be capable of being reshaped. For example, the breast cup 202 may be capable of being reshaped. With respect to the reservoir 204, the reservoir 204 can be resilient in that the reservoir 204 can comprise an initial shape and the reservoir 204 may be capable of being compressed and released and return to the initial shape.

In an embodiment, the breast cup 202 can be applied to a mother's breast to expel breast milk from the breast through the opening 206 into the reservoir 204. Applying the breast cup 202 to the breast and compressing and releasing the reservoir 204 creates an initial suction force to the mother's breast, which enables breast milk to be collected in the reservoir 204. For example, the breast cup 202 may be applied to a mother's breast and the reservoir 204 compressed and released to create an initial suction force. In some embodiments, the initial suction force created may catch breast milk during "let-down" or other breast milk leaks while a child nurses on her other breast.

In some embodiments, the reservoir 204 may continue to be compressed and released to create more suction force beyond the initial suction force to expel more breast milk. For example, the breast cup 202 may be applied to a mother's breast and the reservoir 204 compressed and released to create an initial suction force, and while the mother nurses a child on her other breast, the reservoir 204 may be compressed and released periodically to create more suction pressure to expel more breast milk beyond just breast milk during "let-down" or other breast milk leaks while the child nurses. Additionally or alternatively, the breast cup 202 may be applied to a mother's breast and the reservoir 204 compressed and released to create an initial suction force when mother is not nursing a child on her other breast, and the reservoir 204 may be compressed and released periodically to create more section pressure than just the initial suction force so as to expel breast milk from the breast.

Figure 3:
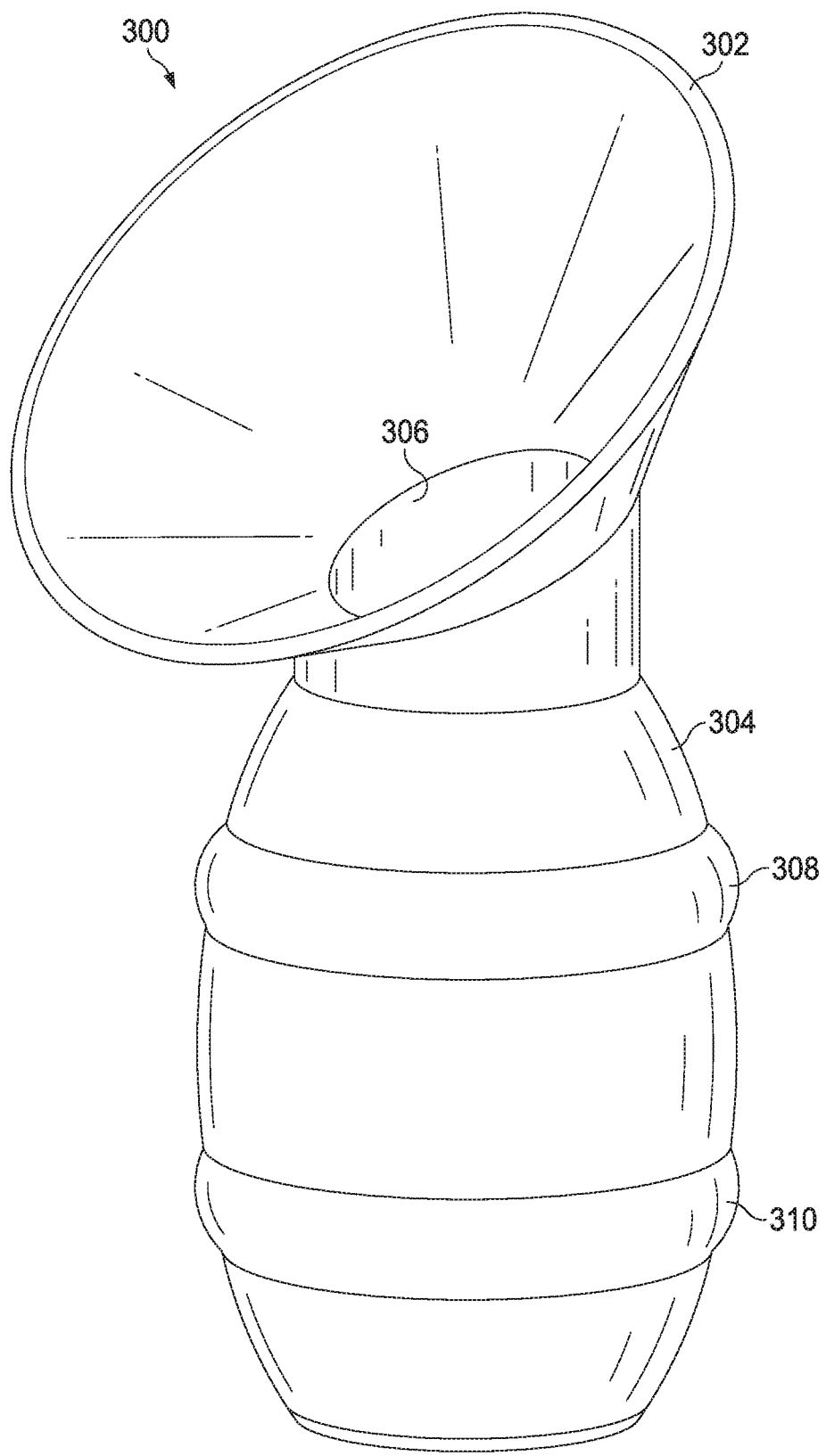
FIG. 3 illustrates a perspective view of a manual breast pump according to another embodiment of the disclosure.

Turning now to FIG. 3, an alternative embodiment of a manual breast pump 300 having a breast cup 302 and a reservoir 304 is illustrated. The manual breast pump 300 of FIG. 3 is similar to the manual breast pump 102 except that the manual breast pump 300 also comprises one or more rings 308, 310 around the perimeter of the reservoir 304. Since the breast cup 302, the reservoir 304, and the opening 306 of the manual breast pump 300 are substantially similar to the breast cup 202, the reservoir 204, and the opening 206 of the manual breast pump 102 discussed above in regard to FIG. 1, only the one or more rings 308, 310 will be addressed below.

In an embodiment, as mentioned above, the reservoir 304 comprises one or more rings 308, 310 around the perimeter of the reservoir 304. For example, the reservoir 304 may comprise only a first ring 308, only a second ring 310, or both the first ring 308 and the second ring 310. In other embodiments, the reservoir 304 may comprise more than two rings. The first ring 308 may be located towards the top of the reservoir 304. The second ring 310 may be located towards the bottom of the reservoir 304. The rings may be made of silicone. For example, the rings 308, 310 (and any additional optional rings, etc.) can be integrally formed with the material of the reservoir 304. The first rings 308 and/or the second ring 310 may add additional thickness to the wall of the reservoir 304 to help vary the suction force due to a changing restoring force. In an embodiment, the wall of the reservoir 304 including the second ring 310 can comprise the thickest cross-section of the reservoir 304 to prevent a bottom of the reservoir 304 from being deformed after the reservoir 304 is compressed.

Figure 4:
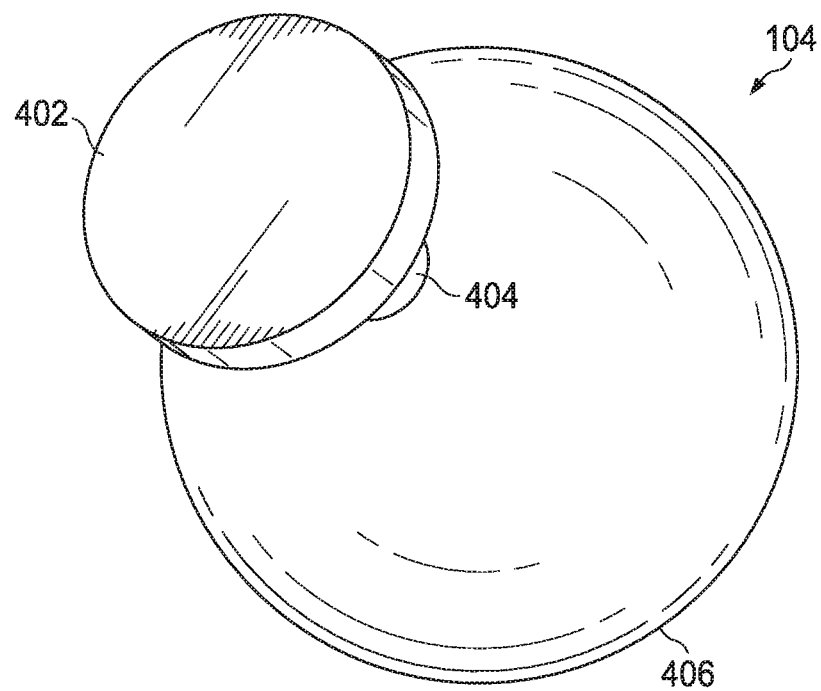
FIG. 4 illustrates a perspective view of a stopper according to an embodiment of the disclosure.
Figure 5:
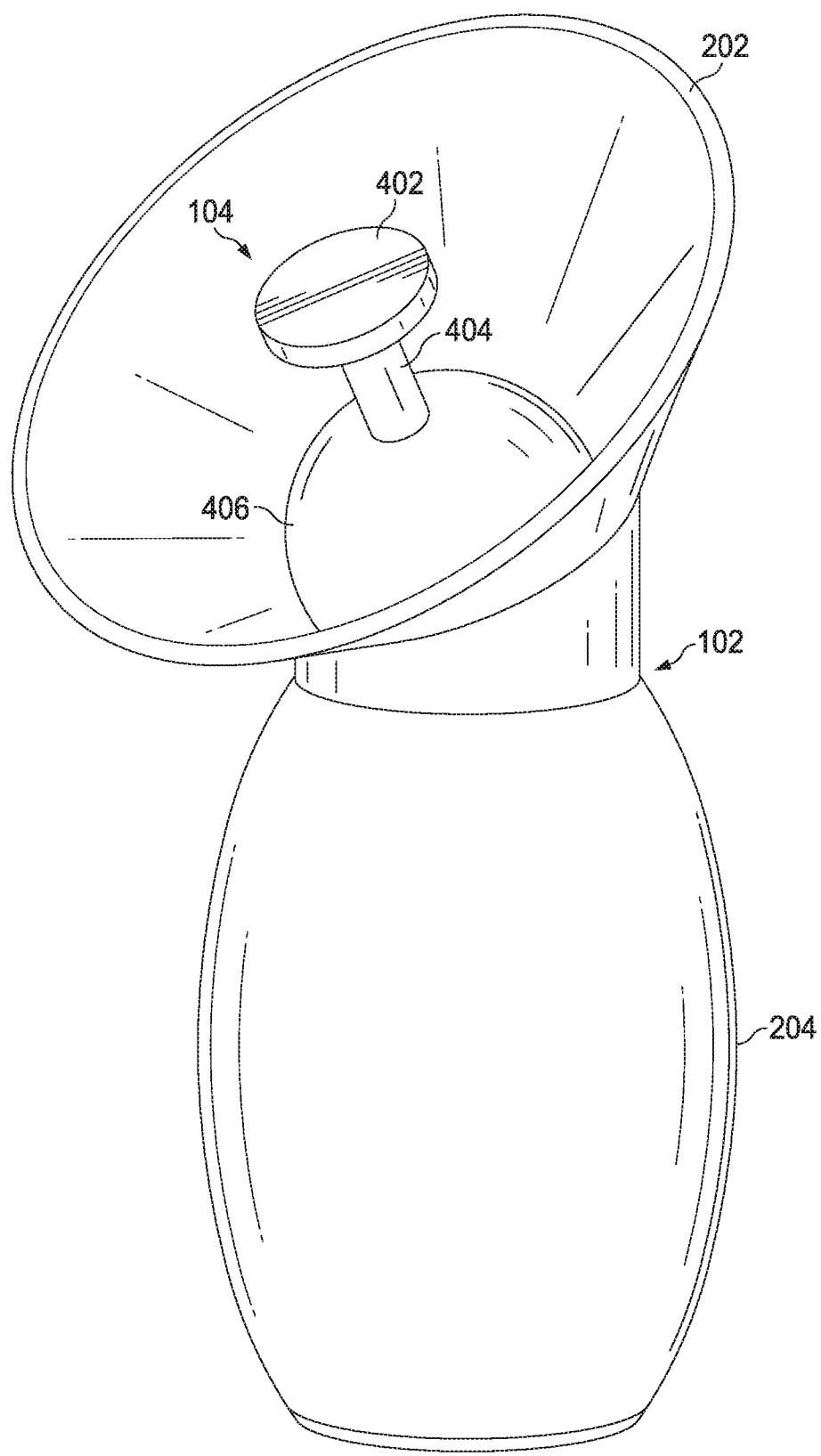
FIG. 5 illustrates a perspective view of a stopper inserted into a manual breast pump according to an embodiment of the disclosure.
Figure 6A:
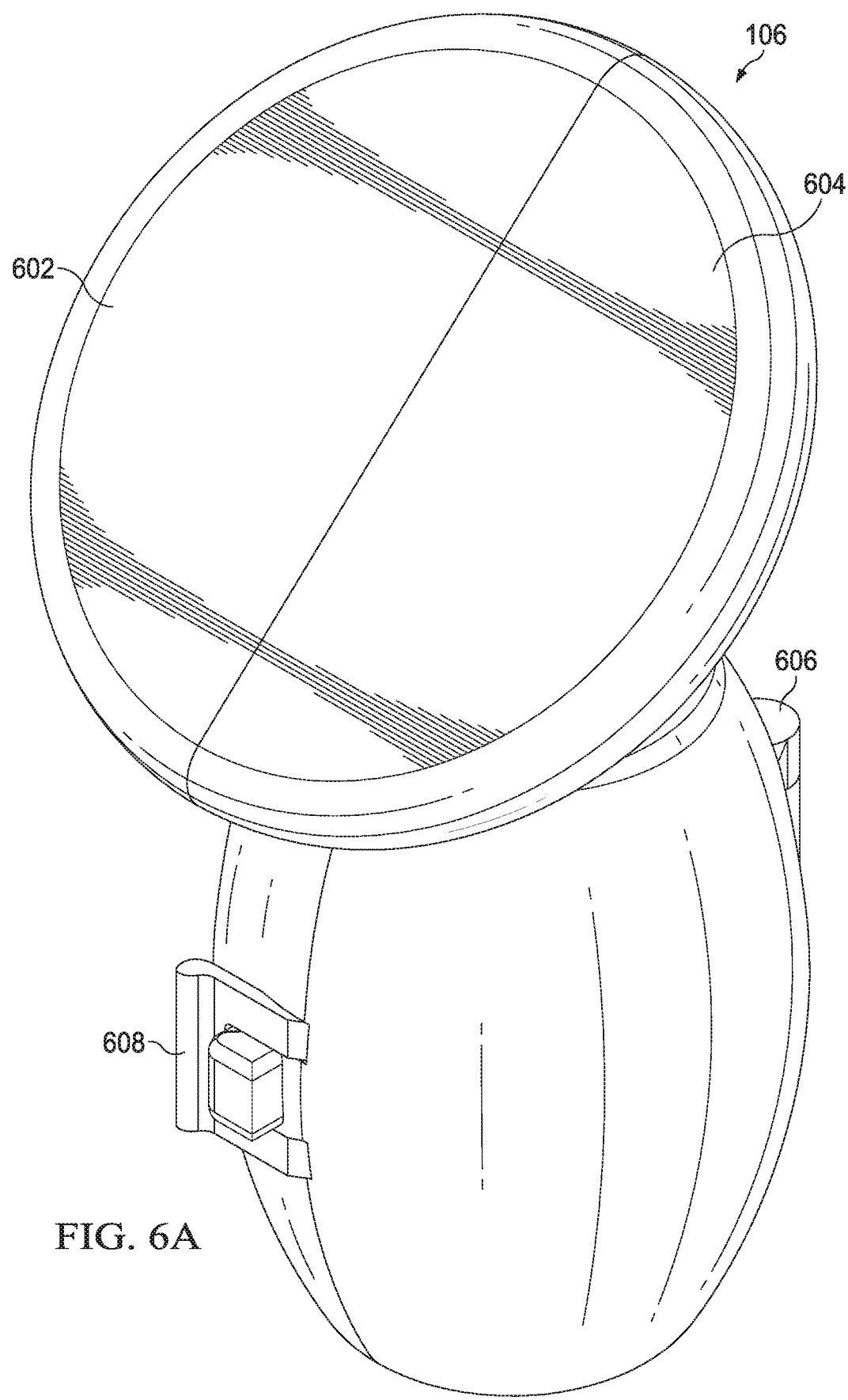
FIG. 6A illustrates a front perspective view of a capsule according to an embodiment of the disclosure.
Figure 6B:
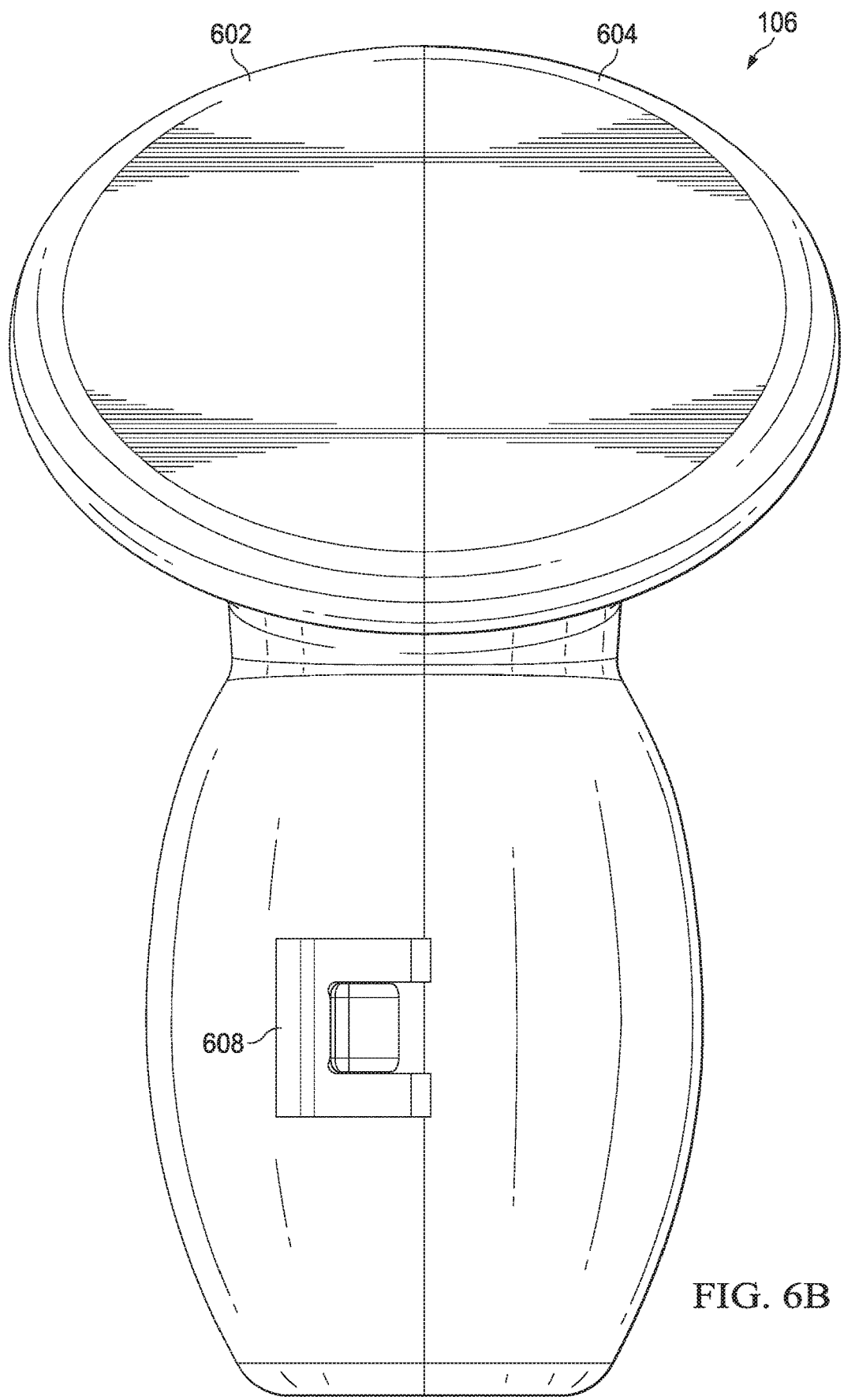
FIG. 6B illustrates a front elevation view of a capsule according to an embodiment of the disclosure.
Figure 6C:
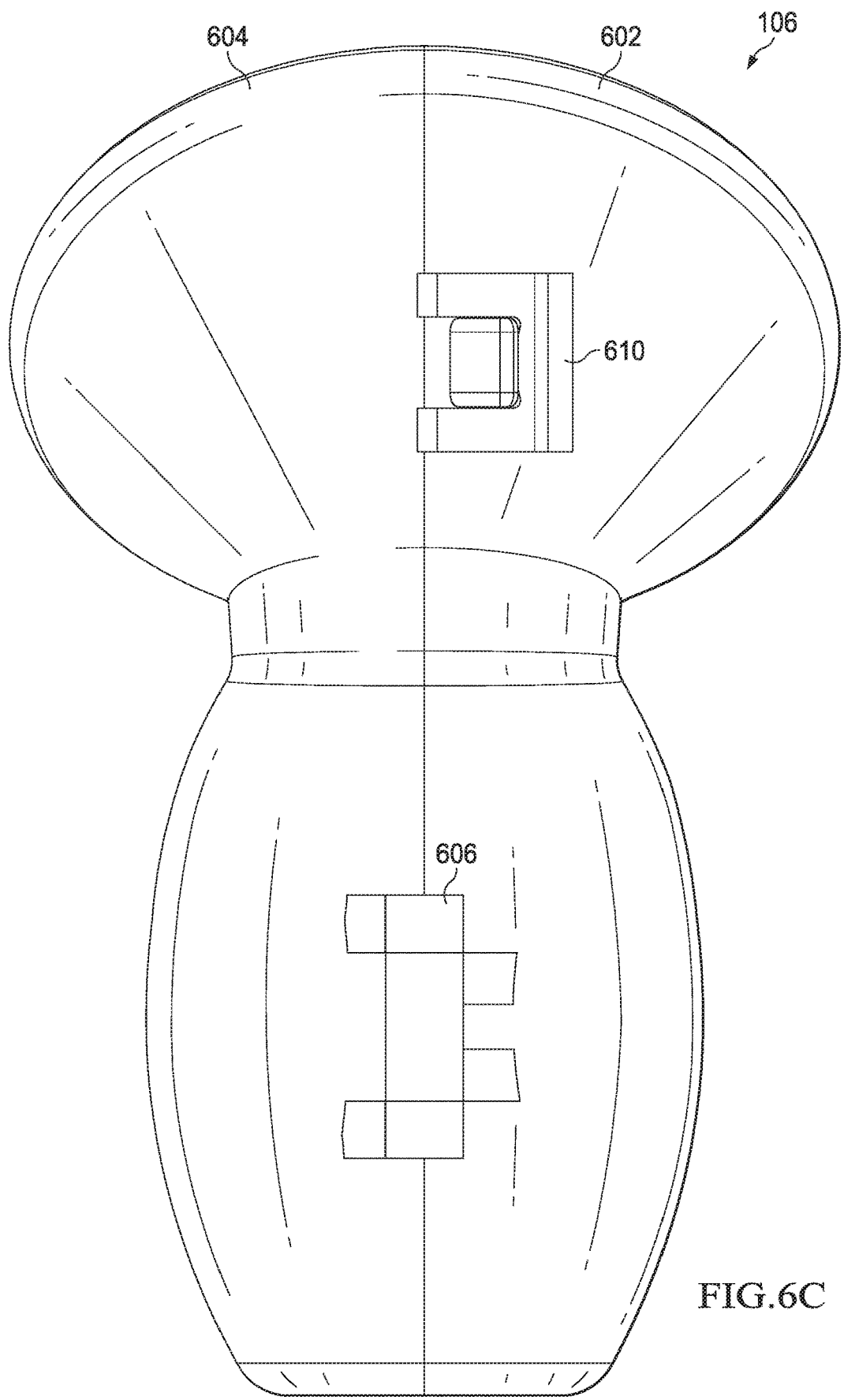
FIG. 6C illustrates a rear elevation view of a capsule according to an embodiment of the disclosure.
Figure 6D:
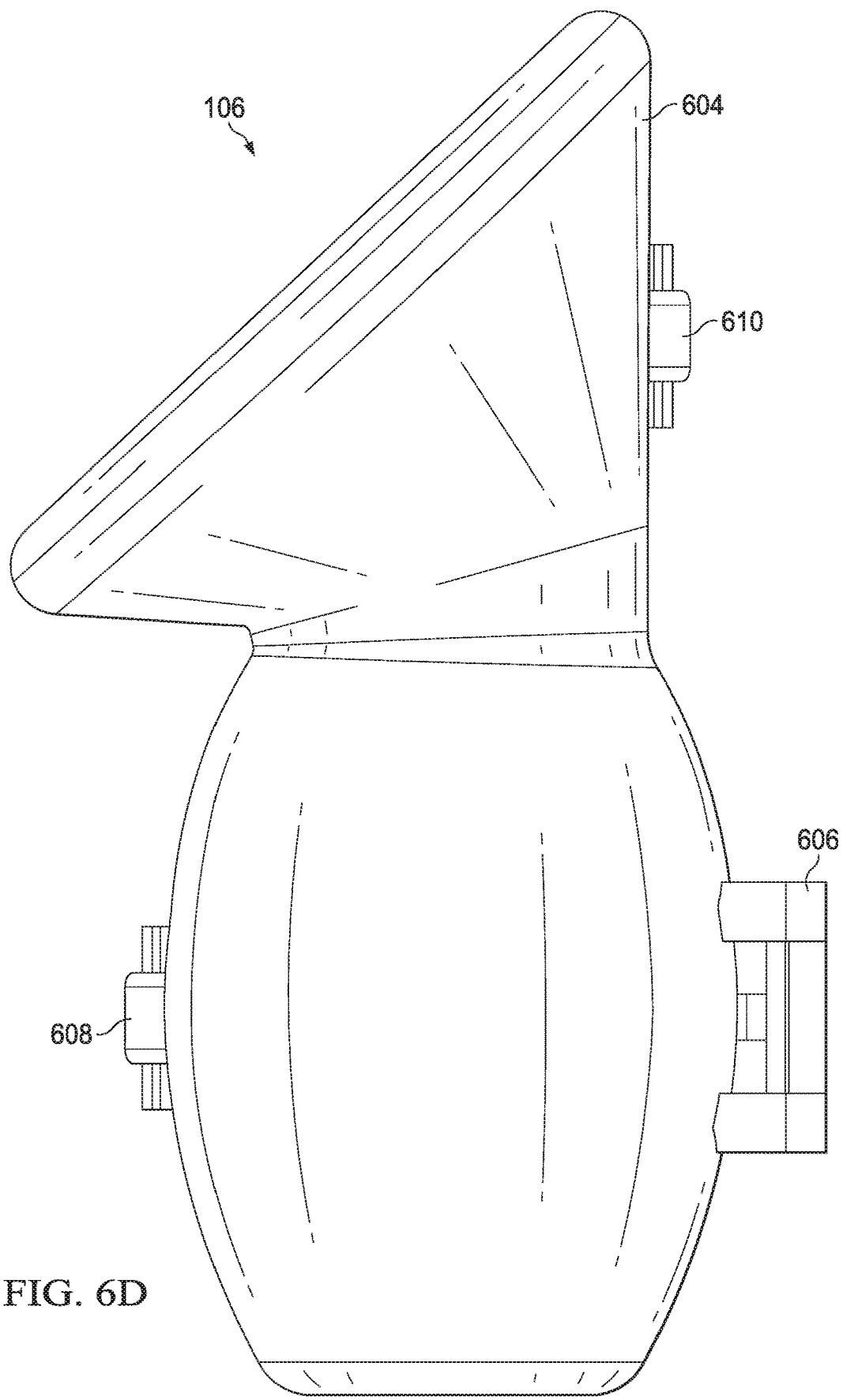
FIG. 6D illustrates a right side view of a capsule according to an embodiment of the disclosure.
Figure 6E:
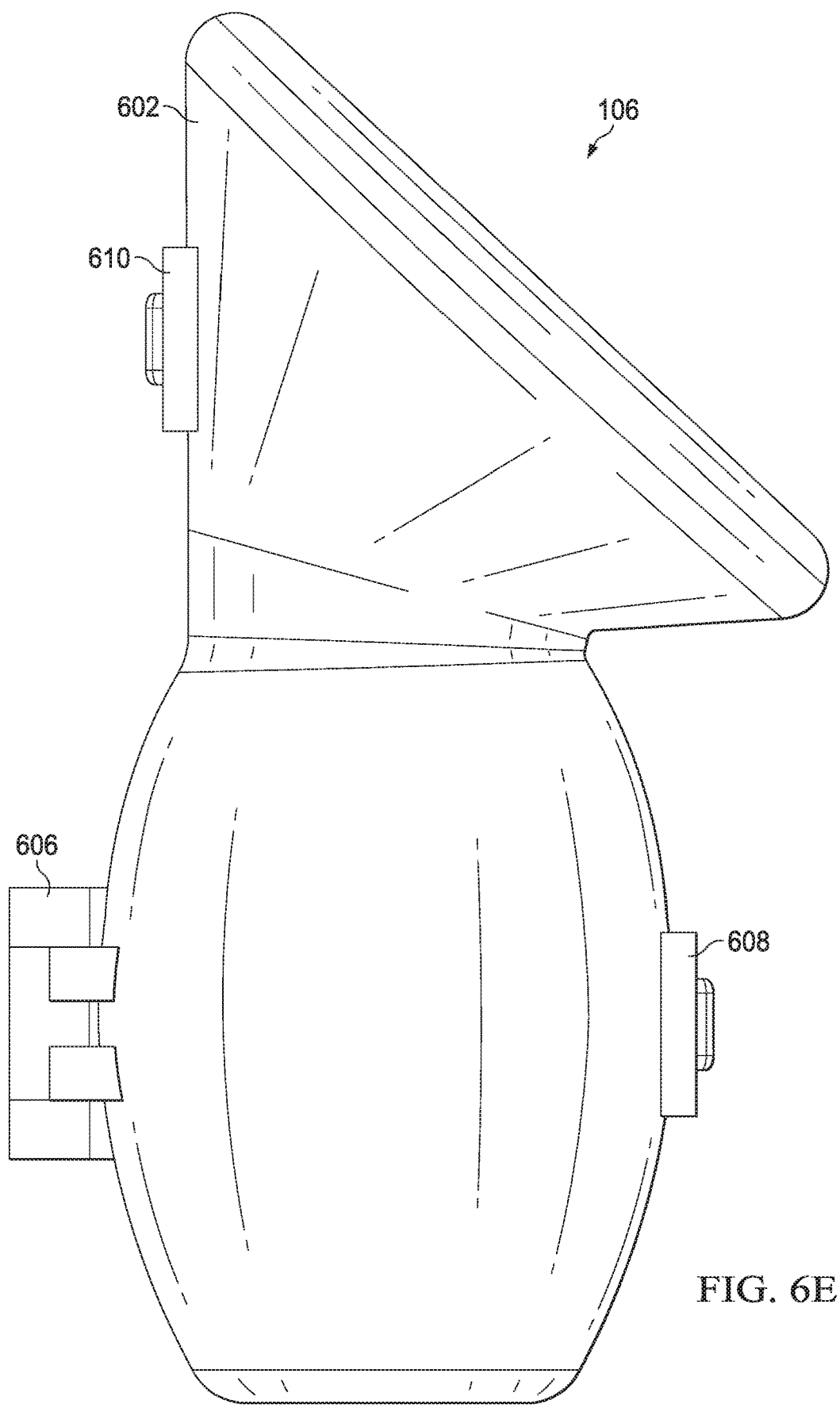
FIG. 6E illustrates a left side view of a capsule according to an embodiment of the disclosure.

Turning now to FIGS. 4 and 5, an embodiment of the stopper 104 is illustrated. The stopper 104 serves to engage with the opening in the manual breast pump 102 and seal the opening to retain the milk in the manual breast pump 102. The stopper may comprise a handle 402, a stem 404, and a sealing surface 406. The handle 402 may be configured to enable a user to more easily insert and remove the stopper 104 from the manual breast pump 102. In an embodiment, the handle is circular in shape. In other embodiments, the handle may be triangular, rectangular, or a different shape. The handle 402 may be coupled to the sealing surface 406 via the stem 404. In an embodiment, the stem 404 comprises a length such that a compression force is applied to the stopper 104 when the capsule 106 is closed.

As illustrated in FIG. 5, the stopper 104 may be inserted into the opening 206 of the breast cup 202. The sealing surface 406 may be of a size and shape to create a seal of the opening 206 to prevent leakage of the breast milk from the reservoir 204. For example, the sealing surface 406 may comprise a rounded shape such as when the opening 206 is circular in shape. The sealing surface 406 may comprise a different shape if the opening 206 is a different shape. While the bottom edge of the sealing surface 406 may illustrated as being uniform, the bottom edge could comprise a non-uniform shape (zig-zagged, scalloped, etc.) without departing from the spirit or scope of the present disclosure. In an embodiment, the sealing surface 406 can be hollow on the inside, which may allow the sealing surface 406 to compress when inserted into the opening 206.

The stopper 104 may be made of pliable or resilient material such as a polymer. Various food grade polymers can be used such as silicone. The material used to form the stopper 104 may have any color or patterns as desired. The material of the stopper 104 can be selected to allow the resilient forces on the sealing surface, when compressed into the opening 206, to form a seal and retain the stopper 104 in position within the opening 206.

Turning now to FIGS. 6A-6E, an embodiment of the capsule 106 is illustrated. The capsule 106 can serve as a container for the manual breast pump 102 that can help to prevent any compression of the manual breast pump during transport, keep the manual breast pump 102 clean, and also aid in retaining the stopper 402 in sealing engagement with the opening 206 of the manual breast pump 102 during transportation. In an embodiment, the capsule 106 is a clamshell type container comprising a first half 602 and a second half 604 joined together by a hinge 606. While only one hinge is illustrated in FIGS. 6A-6E, the capsule 106 may comprise a plurality of hinges.

The capsule 106 may also comprise one or more latches. For example, the capsule 106 may comprise a first latch 608. The first latch 608 may be located on an opposite side of the capsule from the hinge 606. In some embodiments, the capsule may also comprise a second latch 610. The second latch 610 may be located above the hinge 606 on the same axis as the hinge 606. The one or more latches of the capsule 106 may comprise any device in which mating mechanical parts engage to fasten the first half 602 to the second half 604, thereby closing the capsule 106. This can include a closure mechanism relying on a friction fit between the first and second halves of the capsule when closed. While two latches are illustrated in FIGS. 6A-6E, in some embodiments, the capsule 106 may comprise a single latch or more than two latches.

The capsule 106 may be made of stiffer material than the manual breast pump 102. For example, the capsule 106 may be made of a hard plastic. Constructing the capsule 106 out of such a material helps to protect the manual breast pump 102 and prevent leakage of breast milk from the manual breast pump 102 by ensuring that the manual breast pump 102 with the stopper 104 inserted will not be compressed while enclosed in the capsule 106. The material used to form the capsule 106 may have any color or patterns as desired, and in some embodiments may be clear. This may allow the volume of collected breast milk to be determined even when the manual breast pump 102 is enclosed in the capsule 106.

Figure 7:
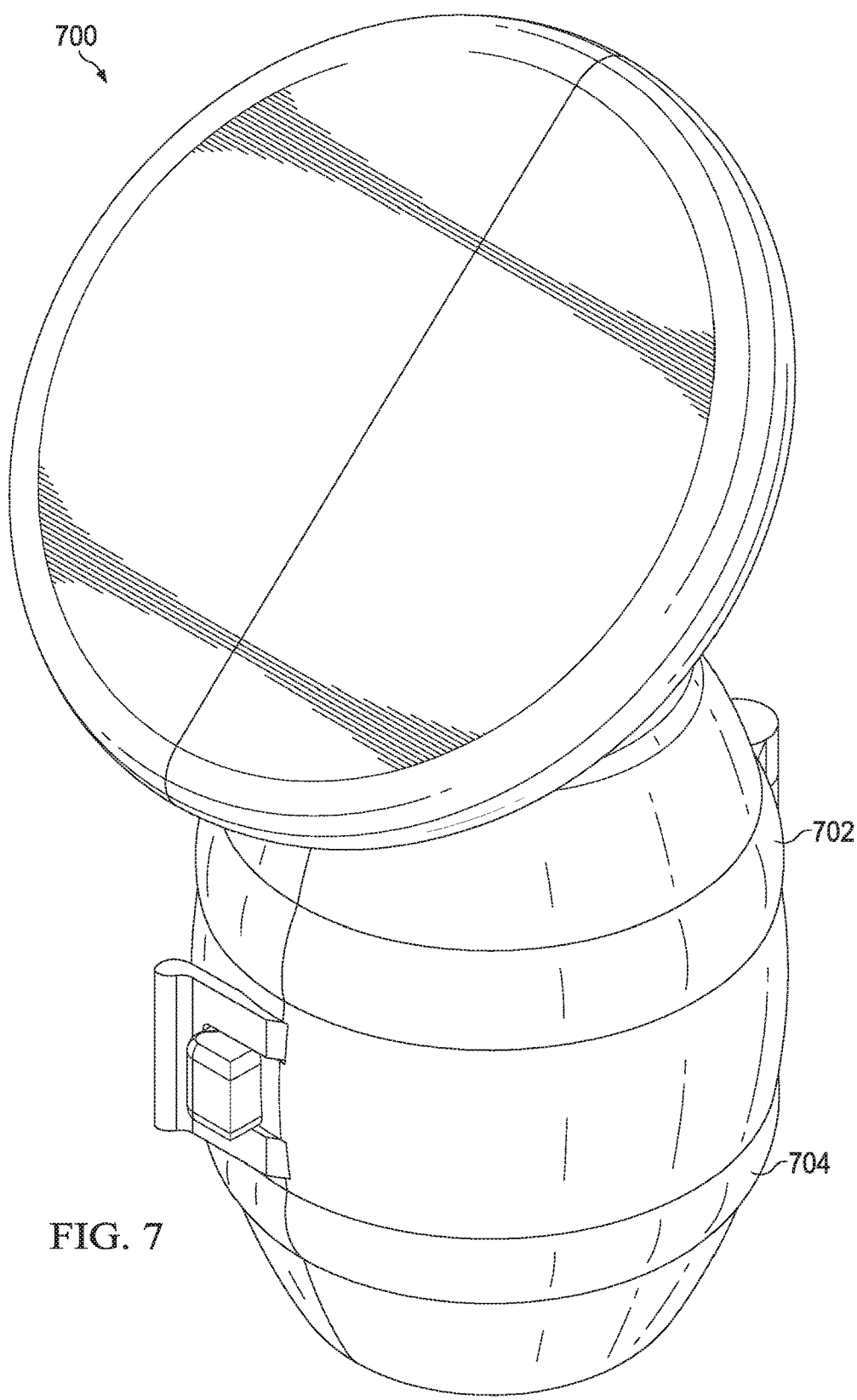
FIG. 7 illustrates a front perspective view of a capsule according to another embodiment of the disclosure.

In an embodiment, the capsule 106 may comprise a shape that corresponds to the shape of a manual breast pump to allow the manual breast pump to be enclosed within and carried with the capsule 106. For example, as illustrated in FIGS. 6A-6E, the capsule 106 may mirror (e.g., correspond to, reflect, etc.) the shape of the manual breast pump 102. In another example, as illustrated in FIG. 7, a capsule 700 may comprise rings 702, 704 for use in combination with manual breast pump 300, which can comprise rings 308, 310. In other embodiments, the capsule 106 may not directly mirror the shape of the manual breast pump 102 (e.g., the capsule 106 may be used in combination with the manual breast pump 300 and/or the capsule 700 may be used in combination with the manual breast pump 102) or the capsule 106 may comprise a different shape than the manual breast pump 102. In an embodiment, the capsule 106 comprises a size such that a compression force is applied to the stopper 104 when the manual breast pump 102 and the stopper 104 inserted therein are enclosed in the capsule 106.

While illustrated in FIGS. 6A-6E and FIG. 7 as a clamshell container that comprises two halves divided vertically that open about a vertical axis, the capsule 106 may instead comprise to halves divided horizontally that open about a horizontal axis. In some embodiments, other constructions of the capsule 106 are possible other than a clamshell container without departing from the spirit or scope of the present disclosure. For example, the capsule 106 could comprise a container with a detachable lid.

Figure 8:
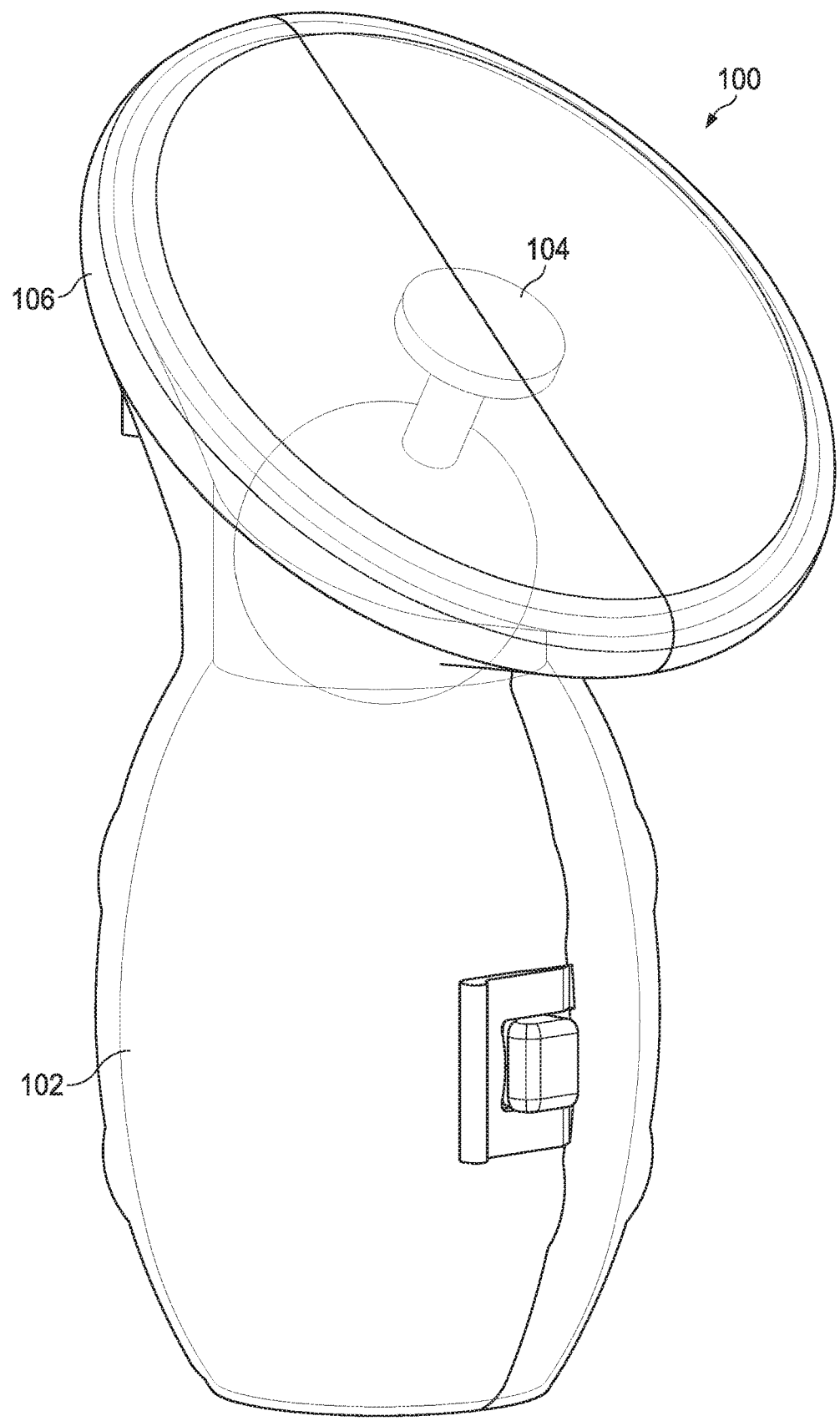
FIG. 8 illustrates a perspective view of a breast milk collection and storage system with a manual beast pump and a stopper closed in a capsule according to an embodiment of the disclosure.

Turning now to FIG. 8, an embodiment of a breast milk collection and storage system 100 is illustrated with the manual breast pump 102 and the stopper 104 closed in the capsule 106. Enclosing the manual breast pump 102 with the stopper inserted 104 in the capsule 106 helps to prevent the stopper 104 from becoming dislodged from the opening 206 of the breast cup 204 and to maintain the seal of the opening 206. As discussed above, construction of the capsule 106 out of a stiffer material than the manual breast pump 102 helps to ensure that the manual breast pump 102 will not be compressed causing the stopper 104 to become dislodged from the opening 206 while the capsule 106 is closed. In some embodiments, the capsule 106 may apply a compression force to the stopper 104 when the capsule 106 is closed such that the stopper 104 is biased into sealing contact with the opening in the manual breast pump while the capsule 106 remains closed. Such a compression force on the stopper 104 helps to further maintain the seal of the opening 206 and prevent the leakage of the breast milk from the manual breast pump 102. The enclosure of the manual breast pump 102 within the capsule 106 as illustrated in FIG. 8 also helps to keep the manual breast pump 102 clean be minimizing its exposure to elements in the environment.

Figure 9:
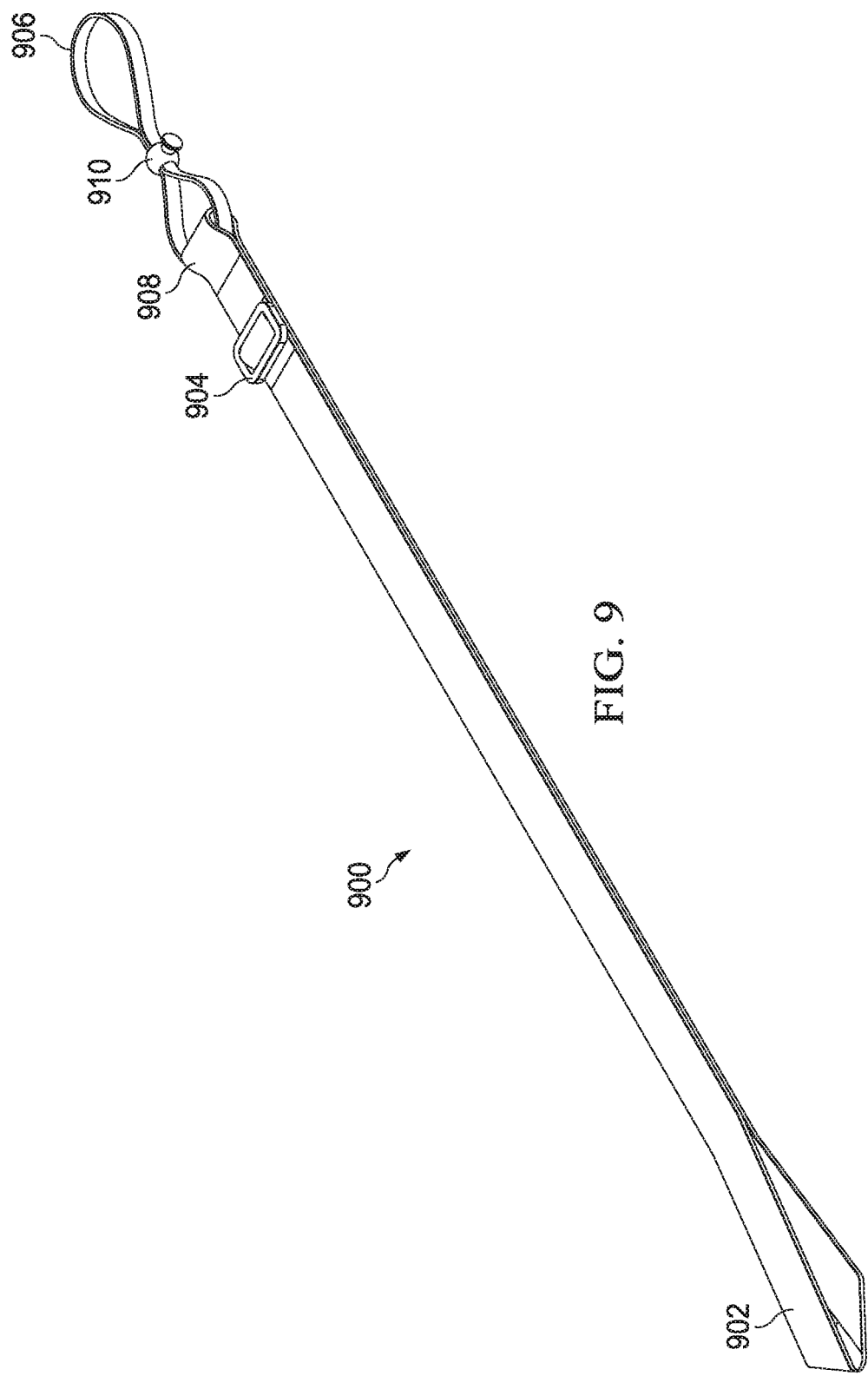
FIG. 9 illustrates a perspective view of a strap according to an embodiment of the disclosure.

Turning now to FIG. 9, an embodiment of a strap 900 is illustrated. In some embodiments, the strap 900 may be a part of the breastmilk collection and storage system 100. The strap 900 may be used by a mother to help prevent leakage of breast milk from the manual breast pump 102 during use of the manual breast pump 102. For example, the strap 900 may secure the manual breast pump 102 to the mother during use so that the manual breast pump 102 does not drop from the mother's breast and leak breast milk from the manual breast pump 102. The strap 900 may flexibly be sized to secure not only the neck of the current embodiment of the manual pump 102 but also accommodate the necks of different pumps with different sizes and capacities (e.g., a 150-200 ml reservoir).

Figure 10:
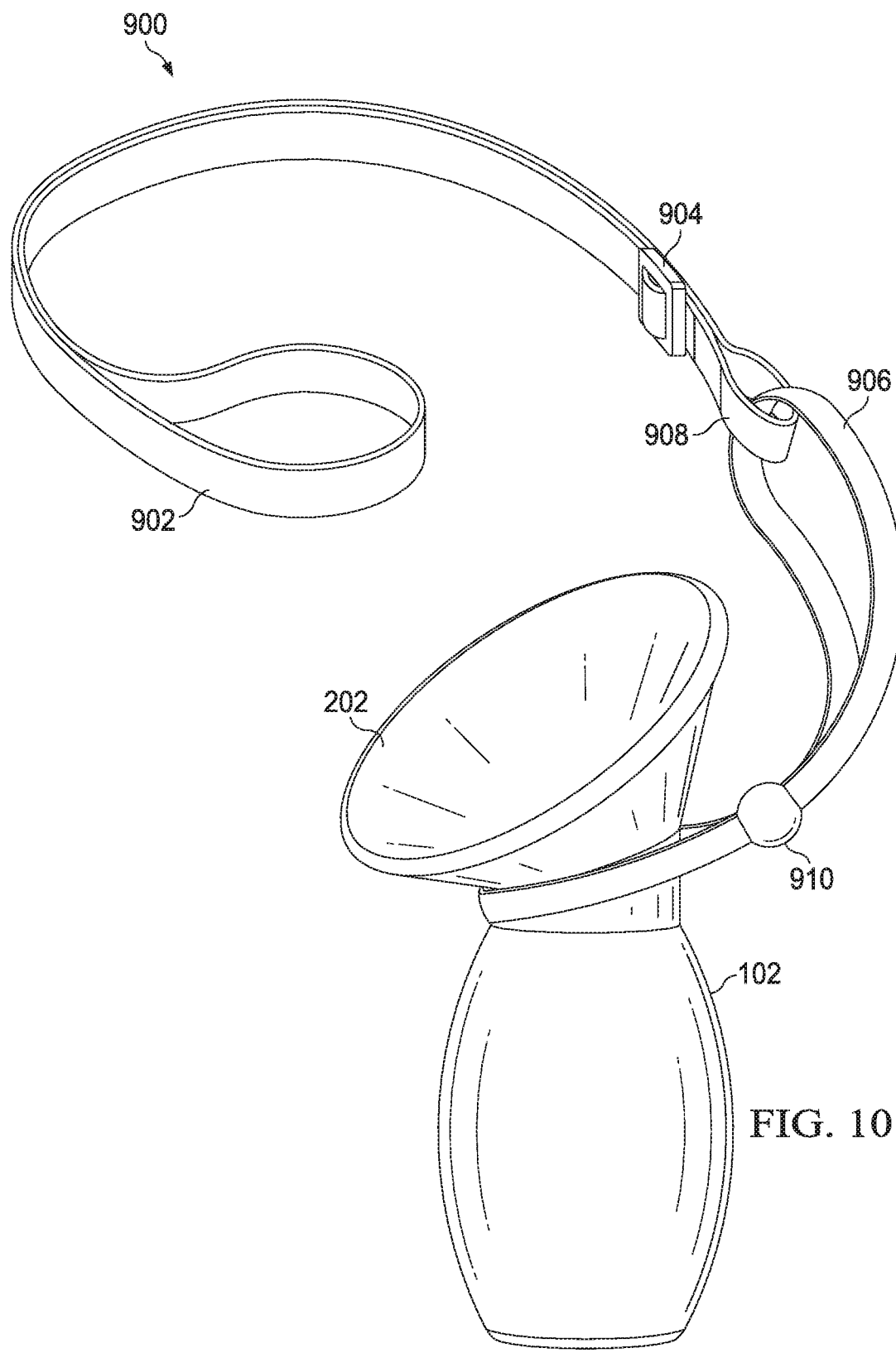
FIG. 10 illustrates a perspective view of a manual breast pump with a strap around the manual breast pump according to an embodiment of the disclosure.

The strap 900 may comprise a main strap 902. The main strap 902 may comprise a slider 904 to enable adjustment of the size of the main strap 902. The strap 900 may also comprise a second strap 906 that is coupled to the main strap 902. As illustrated in FIGS. 9 and 10, the second strap 906 may couple to the main strap 902 by wrapping an end of the main strap 902 around the second strap 906 and securing the end of the main strap 902 to itself so as to form an end loop 908 on one end of the main strap 902. Alternatively, the second strap 906 may couple to the main strap 902 by inserting an end of the second strap 906 through the end loop 908 of the main strap 902 and then securing the ends of the second strap 906 together to form the second strap 906. The second strap 906 may comprise a fastener 910. As illustrated in FIG. 10, the fastener 910 may be configured to secure the second strap 906 around the base of the breast cup 202.

In an embodiment, the fastener 910 comprises a cord lock. The cord lock may comprise a barrel, a toggle, and a spring. When the toggle is pushed down toward the barrel, tension from the spring may be released and the cord lock can move freely on the second strap 906. When the toggle is released, the tension from the spring may be engaged and the cord lock remains in place on the second strap 906. While the fastener 910 is illustrated as a cord lock in FIG. 9 and FIG. 10, the fastener 910 may comprise a different type of fastener without departing from the spirit or scope of the present disclosure.

The strap 900 may be made of one or more materials. For example, the strap 900 may be made of cotton, jersey, silk, linen, nylon, polyester, leather, and/or another material. In some embodiments, the main strap 902 and the second strap 906 may be made of different material.

A mother may use the strap 900 to prevent the manual breast pump 102 from dropping from the breast while in use such as when a baby kicks the manual breast pump while nursing on the other breast. To use the strap 900, the main strap 902 may be placed around the neck of the mother. The main strap 902 can be adjusted via the slider 904 to align the breast cup 202 with the mother's breast. The second strap 906 may be placed around the base of the breast cup 202 and secured around the base of the breast cup 202 by moving the fastener 910 toward the base of the breast cup 202. If the manual breast pump 102 becomes disengaged from the mother's breast during use, the manual breast pump 102 will still be secured to the mother via the main strap 902, thereby preventing leakage of breast milk from the manual breast pump 102.

A mother may alternatively or additionally use the strap 900 to carry or transport the manual breast pump 102 and/or the capsule 106 between uses. For example, the main strap 902 may be placed around an arm or shoulder of the mother and the second strap 906 may be placed around the base of the breast cup 202 and secured by moving the fastener 910 toward the base of the breast cup 202. In another example, the main strap 902 may be placed around an arm or shoulder of the mother and the second strap 906 may be placed around the neck of the capsule 106 and secured by moving the fastener 910 toward the neck of the capsule 106. In some embodiments, the second strap 906 may also help maintain the closure of the capsule 106 when the second strap 906 is secured around the neck of the capsule 106.

A mother may alternatively or additionally use the strap 900 to secure the manual breast pump 102 and/or the capsule 106 to another object between uses. For example, the mother may use the strap 900 to secure the manual breast pump 102 and/or the capsule to a chair, a strap of their purse or baby bag, or to another object.

The manual breast pump 102, the stopper 104, the capsule 106, and/or the strap 900 may be sold individually or as a group. In an embodiment, the manual breast pump 102, the stopper 104, and the capsule 106 are sold as a kit. In some embodiments, the kit may also comprise the strap 900.

Figure 11:
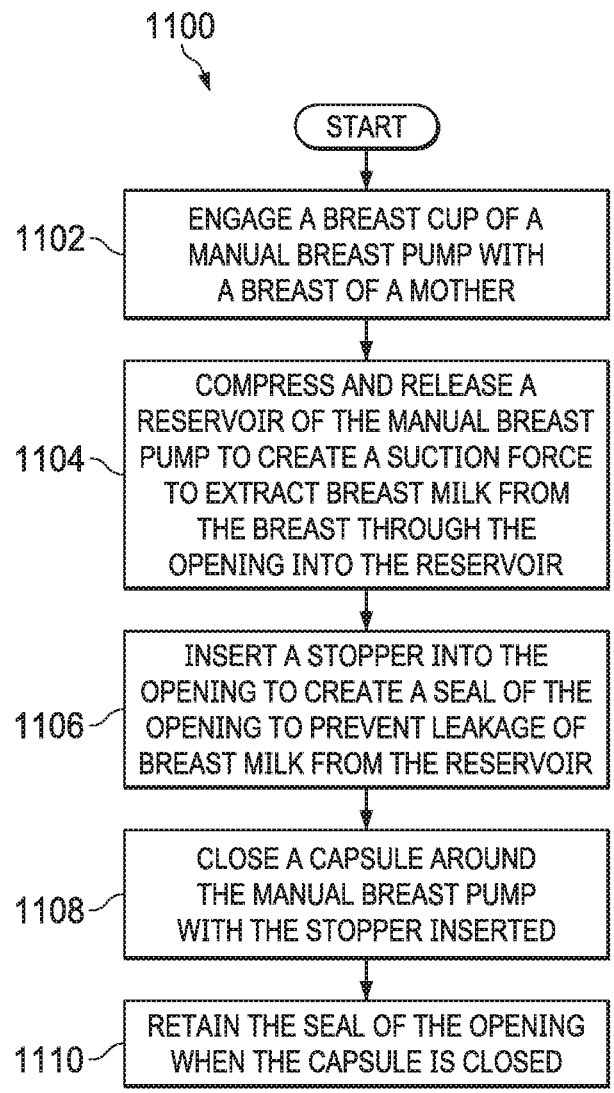
FIG. 11 illustrates a flow chart of a method according to an embodiment of the disclosure.

Turning now to FIG. 11, a method 1100 is described. At block 1102, a breast cup of a manual breast pump is engaged with a breast of a mother. The breast cup comprises an opening. At block 1104, a reservoir of the manual breast pump is compressed and released to create a suction force to extract breast milk from the breast through the opening into the reservoir. At block 1106, a stopper is inserted into the opening to create a seal of the opening to prevent leakage of breast milk from the reservoir. At block 1108, a capsule is closed around the manual breast pump with the stopper inserted. The closing of the capsule can apply a compressive force on the stopper such that the stopper is biased into sealing engagement with the opening in the manual breast pump when the capsule is closed. At block 1110, the seal of the opening is maintained when the capsule is closed. The sealing of the opening can be based on the compressive force provided by the closed capsule such that the opening can remain sealed while the capsule is closed. Further, the closed capsule may also prevent any compressive forces from being applied to the manual breast pump while closed. This can help to avoid the generation of pressure within the manual breast pump that could dislodge the stopper or cause milk to leak.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit or scope of the present disclosure.

What is claimed is:

1. A breast milk collection and storage system, comprising:
   a manual breast pump that comprises:
      a breast cup configured to engage with a mother's breast, the breast cup comprising an opening; and
      a reservoir at a base of the breast cup configured to receive breast milk through the opening and collect the breast milk extracted from the mother's breast;
   a stopper configured to seal the opening to prevent leakage of the breast milk from the reservoir; and
   a capsule configured to enclose the manual breast pump with the stopper and apply a compression force to the stopper to maintain the seal of the opening when the capsule is closed.

2. The breast milk collection and storage system of claim 1, wherein the capsule comprises:
   two halves joined by at least one hinge; and
   one or more latches.

3. The breast milk collection and storage system of claim 2, wherein the capsule comprises a shape substantially similar to a shape of the manual breast pump.

4. The breast milk collection and storage system of claim 2, wherein the one or more latches comprise a first latch on a same axis as the at least one hinge and a second latch on an opposite side of the capsule from the at least one hinge and the first latch.

5. The breast milk collection and storage system of claim 1, wherein the stopper comprises:
   a handle;
   a stem; and
   a sealing surface.

6. The breast milk collection and storage system of claim 5, wherein the stem comprises a length such that the compression force is applied to the stopper when the capsule is closed.

7. The breast milk collection and storage system of claim 1, further comprising a strap configured to encircle the base of the breast cup and prevent the manual breast pump from dropping from the mother's breast while the manual breast pump is in use.

8. The breast milk collection and storage system of claim 7, wherein the strap comprises:
   a main strap configured to be adjustable in size via a slider; and
   a second strap coupled to the main strap at an end of the main strap, wherein the second strap comprises a fastener that is configured to secure the second strap around the base of the breast cup.

9. The breast milk collection and storage system of claim 1, wherein the capsule is made of stiffer material than the manual breast pump.

10. The breast milk collection and storage system of claim 1, wherein the breast cup and reservoir are made of silicone.

11. A method of using a breast milk collection and storage system, the method comprising:
   engaging a breast cup of a manual breast pump with a breast of a mother, wherein the breast cup comprises an opening;
   compressing and releasing a reservoir of the manual breast pump to create a suction force to extract breast milk from the breast through the opening into the reservoir;
   inserting a stopper into the opening to create a seal of the opening to prevent leakage of the breast milk from the reservoir;
   closing a capsule around the manual breast pump with the stopper inserted; and
   retaining the seal of the opening when the capsule is closed, wherein the seal is retained by the capsule applying a compression force to the stopper when the capsule is closed.

12. The method of claim 11, further comprising preventing the manual breast pump from dropping from the breast while compressing and releasing the reservoir by:
   placing a first end of a strap around a neck of the mother;
   placing a second end of the strap around a base of the breast cup; and
   securing the second end of the strap around the base of the breast cup.

13. The method of claim 12, further comprising adjusting the first end of the strap via a slider on the strap to align the breast cup with the breast.

14. The method of claim 12, wherein the second end of the strap is secured around the base of the breast cup by moving a fastener on the second end of the strap toward the base of the breast cup.

15. A breast milk collection and storage kit, comprising:
   a manual breast pump that comprises:
      a breast cup configured to engage with a mother's breast, the breast cup comprising an opening; and
      a reservoir at a base of the breast cup configured to receive breast milk through the opening and collect the breast milk extracted from the mother's breast;
   a stopper configured to seal the opening to prevent leakage of breast milk from the reservoir; and
   a capsule configured to enclose the manual breast pump with the stopper and maintain the seal of the opening, wherein the capsule is configured to maintain the seal by applying a compression force to the stopper when the capsule is closed.

16. The breast milk collection and storage kit of claim 15, wherein the capsule comprises:
   two halves joined by at least one hinge; and
   one or more latches.

17. The breast milk collection and storage kit of claim 15, wherein the capsule comprises a shape substantially similar to a shape of the manual breast pump.

18. The breast milk collection and storage kit of claim 15, further comprising a strap configured to encircle the base of the breast cup and prevent the manual breast pump from dropping from the mother's breast while the manual breast pump is in use.

* * * * *